US00PP19677P2

(12) United States Plant Patent
Valstar

(10) Patent No.: US PP19,677 P2
(45) Date of Patent: Feb. 10, 2009

(54) ***CALATHEA* PLANT NAMED 'HGV07'**

(50) Latin Name: *Calathea*
Varietal Denomination: HGV07

(75) Inventor: Oscar R. Valstar, Maasland (NL)

(73) Assignee: Gebr. Valstar Beheer BV, Maasland (NL)

( * ) Notice: Subject to any disclaimer, the term of this patent is extended or adjusted under 35 U.S.C. 154(b) by 44 days.

(21) Appl. No.: 11/716,739

(22) Filed: Mar. 9, 2007

(51) Int. Cl.
*A01H 5/00* (2006.01)

(52) U.S. Cl. ..... Plt./375

(58) Field of Classification Search ..... Plt./375
See application file for complete search history.

(56) References Cited

PUBLICATIONS

UPOV–ROM GTITM, Plant Variety Database, 2007/04, GTI Jouve Retrieval Software, citation for calathea 'HGV07'.*

* cited by examiner

*Primary Examiner*—Annette H Para
*Assistant Examiner*—S. B. McCormick-Ewoldt

(57) ABSTRACT

A new cultivar of *Calathea* plant named 'HGV07' that is characterized by broad lance shaped leaves that are variegated and have white main veins.

1 Drawing Sheet

Botanical classification: *Calathea*
Variety denomination: 'HGV07'.

BACKGROUND OF THE INVENTION

The present invention relates to a new and distinct cultivar of *Calathea* plant botanically known as *Calathea* and hereinafter referred to by the cultivar name 'HGV07'.

The new cultivar was discovered by the inventor in a cultivated area of Roosendaal, The Netherlands in October of 2004. 'HGV07' was discovered as a naturally occurring branch mutation within a population of unnamed *Calathea* plants.

Asexual reproduction by division of the new cultivar 'HGV07' was first performed in February of 2005 in Roosendaal, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Calathea* cultivar 'HGV07'.

1. *Calathea* 'HGV07' exhibits variegated leaves that have white main veins.
2. *Calathea* 'HGV07' exhibits broad lance shaped leaves.

The closest comparison cultivars are *Calathea* 'Insignis' and 'Makoyana'. The new cultivar 'HGV07' is distinguishable from 'Insignis' by the following characteristics:

1. 'HGV07' has leaves with white main veins.
2. 'HGV07' has wider leaves.

The new cultivar 'HGV07' is distinguishable from 'Makoyana' by the following characteristics:

1. 'HGV07' has leaves with white main veins.
2. 'HGV07' has lance shaped leaves. The leaves of 'Makoyaha' are ovate shaped.

The new cultivar 'HGV07' is distinguishable from the parent plant by the following characteristics:

1. 'HGV07' has leaves with white main veins. The main veins of the parent plant are not white.

BRIEF DESCRIPTION OF THE DRAWING

The accompanying photograph illustrates the distinguishing traits of *Calathea* 'HGV07'. The plant in the photograph shows an overall view of a 30 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Calathea* cultivar named 'HGV07'. Data was collected in Maasland, The Netherlands from 30 week old greenhouse grown plants in 13 cm containers. The time of year was Winter and the average temperature was 21 degrees Centigrade during the day and 20 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'HGV07' has not been tested under all possible conditions and phenotypic differences may be observed with variations in environmental, climatic, and cultural conditions, however, without any variance in genotype.

*Leaf margin.*—Entire, slightly wavy, average 18 waves per leaf. (9 on each side)

*Vein pattern.*—Pinnate.

*Young leaf color (upper surface).*—Margins 146C, Leaf blade yellow-green 146A, with irregularly variegated areas on and in between the secondary veins, this variegation is yellow-green to greyed-green between 150D and 195D.

*Young leaf color* (*lower surface*).—Greyed-orange 176B to 176C, in areas that are variegated on the upper side greyed-red 182B.

*Mature leaf color* (*upper surface*).—Margins green 137A, Leaf blade dark green 139A, with irregularly variegated areas on and in between the secondary veins; this variegation is yellow-green 144A to 144B.

*Mature leaf color* (*lower surface*).—Purple to greyed-orange between N77C and 176B to 176C, in areas that are variegated on the upper side greyed-red 182B.

*Vein color* (*lower surface*).—153D.

*Vein color* (*upper surface*).—145D.

*Leaf attachment.*—Petiolate.

*Petiole dimensions.*—Average 18.8 cm in length including geniculum, 3.7 mm in diameter below geniculum to 4.5 mm in diameter above clump.

*Petiole aspect.*—Rounded.

*Petiole surface.*—Smooth, glossy.

*Petiole color.*—148A, towards the base 176B.

*Geniculum dimensions.*—Average 2.5 cm in length and 4 mm in diameter.

*Geniculum color.*—146C.

*Wing dimensions.*—Average 6.2 cm in length and 3 mm in diameter.

*Wing color.*—176B to 176C.

*Durability of foliage to stress.*—Moderate to high.

Flowers: Flowers have not been observed.

Disease and insect resistance: Plants of the new *Calathea* have not been observed for disease or insect resistance.

Botanical classification: *Calathea* 'HGV07'.

Use: Ornamental.

Parentage: 'HGV07' is a naturally occurring branch mutation of an unknown *Calathea* cultivar.

Vigor: Moderate.

Growth rate: Moderate.

Growth habit: Moderately branching from base.

Plant shape: Globose.

Suitable container size: 13 cm diameter container.

Height: Average 37.5 cm in height.

Width: Average 44 cm in width.

Hardiness: USDA Zone 10.

Propagation: Division.

Number of divisions or clumps per year: 3

Time to produce a rooted cutting: Approximately 10 days in the Summer and Winter.

Time to produce a young plant: Approximately 90 days in the Summer and 110 days in the Winter.

Root system: Thick and fibrous.

Stem: No stems, Leaves grow directly from base, Average 8 clumps.

Foliage:

*Texture.*—Both surfaces smooth, glossy and leathery.

*Leaf arrangement.*—Alternate, growing from the base.

*Compound or single.*—Single.

*Leaf shape.*—Narrow Ovate.

*Leaf apex.*—Short acute.

*Leaf base.*—Obtuse.

*Leaf length.*—Average 20.3 cm in length.

*Leaf width.*—9.5 cm in width.

*Quantity of leaves per clump.*—Average 3.5.

*Pubescence.*—No leaf pubescence.

It is claimed:

1. A new and distinct variety of *Calathea* plant named 'HGV07' as described and illustrated.

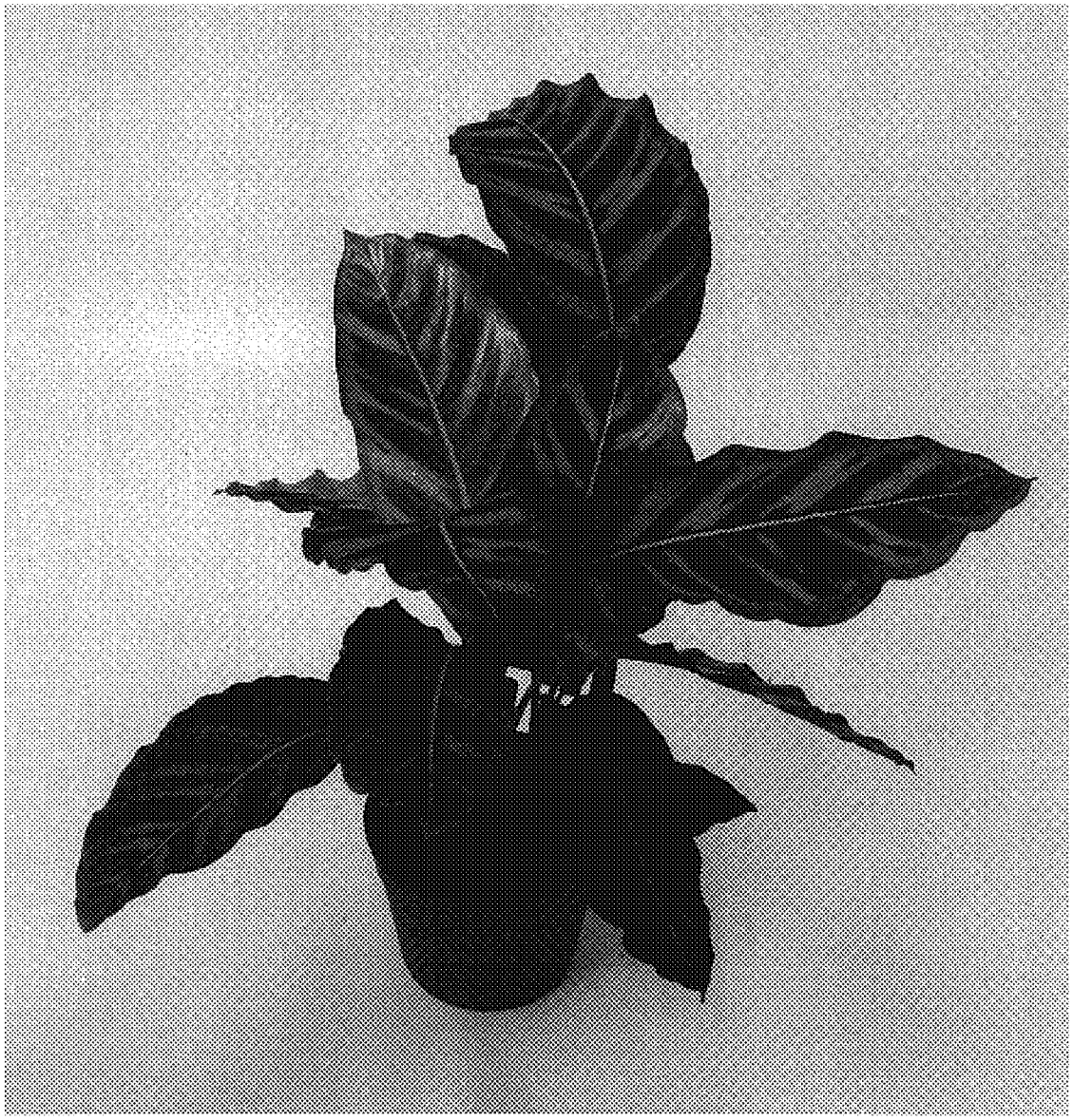

* * * * *